United States Patent
Shih

(10) Patent No.: US 9,404,851 B2
(45) Date of Patent: Aug. 2, 2016

(54) METHOD FOR QUANTITATIVELY MEASURING THE CONCENTRATION OF A COMPOUND OF UNKNOWN CONCENTRATION IN SOLUTION

(71) Applicant: I-Tsung Shih, Basking Ridge, NJ (US)

(72) Inventor: I-Tsung Shih, Basking Ridge, NJ (US)

(73) Assignee: C Technologies Inc, Bridgewater, NJ (US)

( * ) Notice: Subject to any disclaimer, the term of this patent is extended or adjusted under 35 U.S.C. 154(b) by 0 days.

(21) Appl. No.: 14/545,931

(22) Filed: Jul. 9, 2015

(65) Prior Publication Data

US 2016/0011099 A1    Jan. 14, 2016

Related U.S. Application Data

(60) Provisional application No. 61/998,833, filed on Jul. 9, 2014.

(51) Int. Cl.
*G01N 21/25*    (2006.01)
*G01N 21/31*    (2006.01)

(52) U.S. Cl.
CPC .............. *G01N 21/31* (2013.01); *G01N 21/255* (2013.01); *G01N 2021/3129* (2013.01)

(58) Field of Classification Search
CPC ..... G01N 21/31; G01N 21/29; G01N 21/251; G01N 21/255; G01N 21/0303; G01J 21/03; G01J 3/02
USPC .................................................. 356/300–445
See application file for complete search history.

(56) References Cited

U.S. PATENT DOCUMENTS 6,444,641 B1 *    9/2002    Flora ..................... A61K 38/28
                                                                424/185.1

* cited by examiner

*Primary Examiner* — Abdullahi Nur
(74) *Attorney, Agent, or Firm* — G Kennal Smith

(57) ABSTRACT

The present invention relates to methods of spectrophotometric determination of the presence of particular substances in a complex mixture of compounds. This invention relates to methods for determining the concentration of various components of complex biological samples including the determination of the concentration of polyoxyethylene containing compounds including polysorbate in protein containing samples as well as determining the ratio of drug to antibody ratios in antibody-drug conjugate solutions.

14 Claims, 5 Drawing Sheets

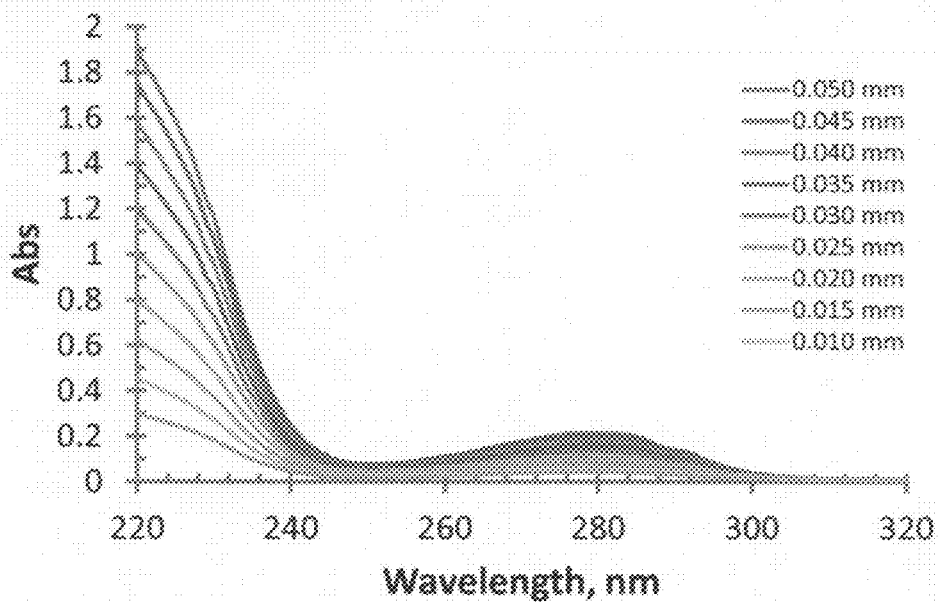
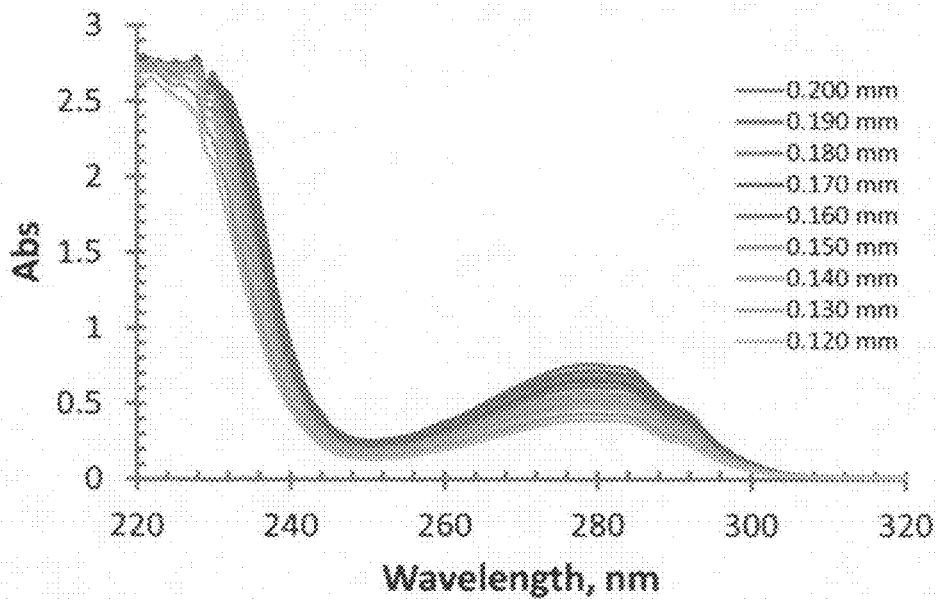

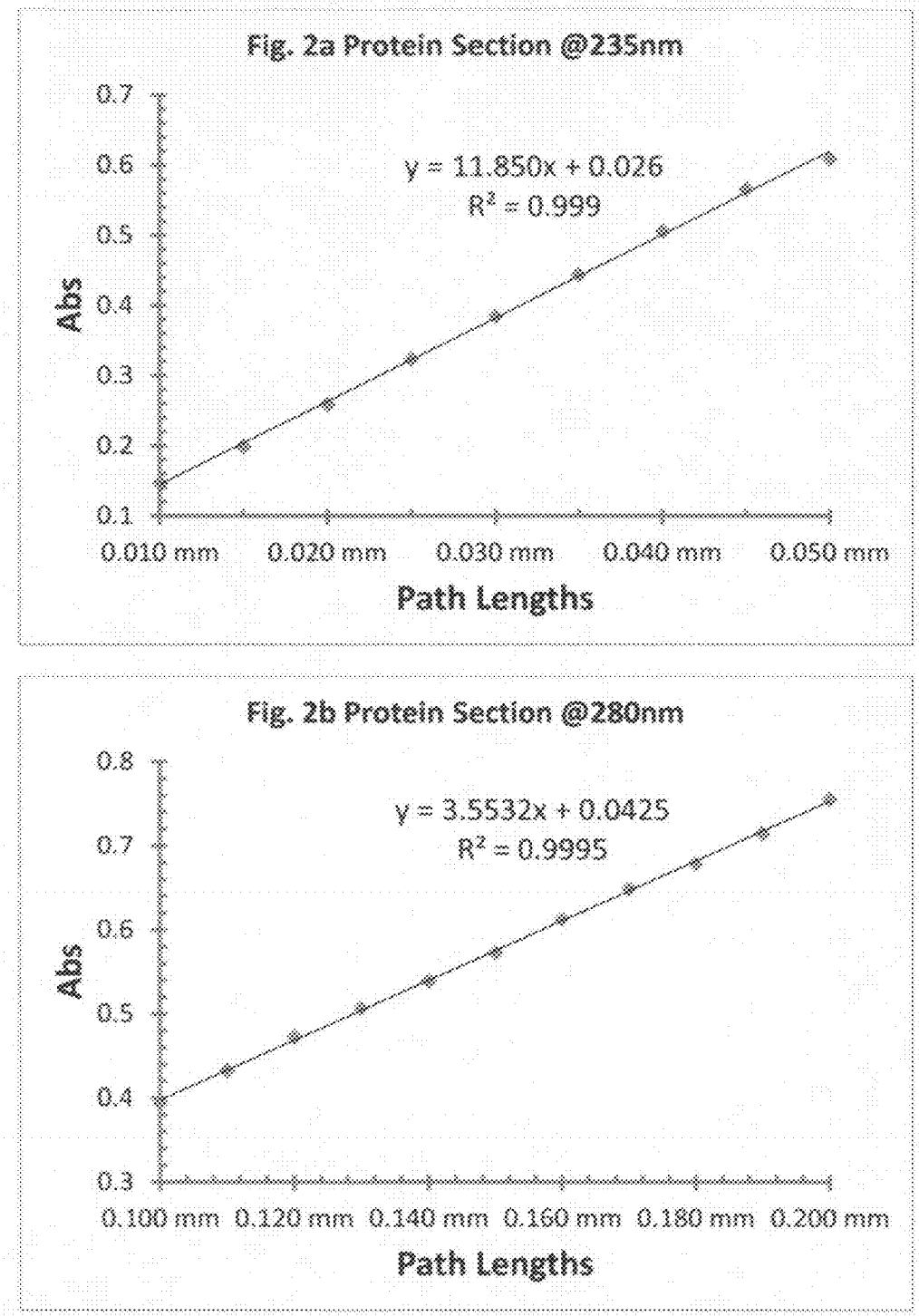

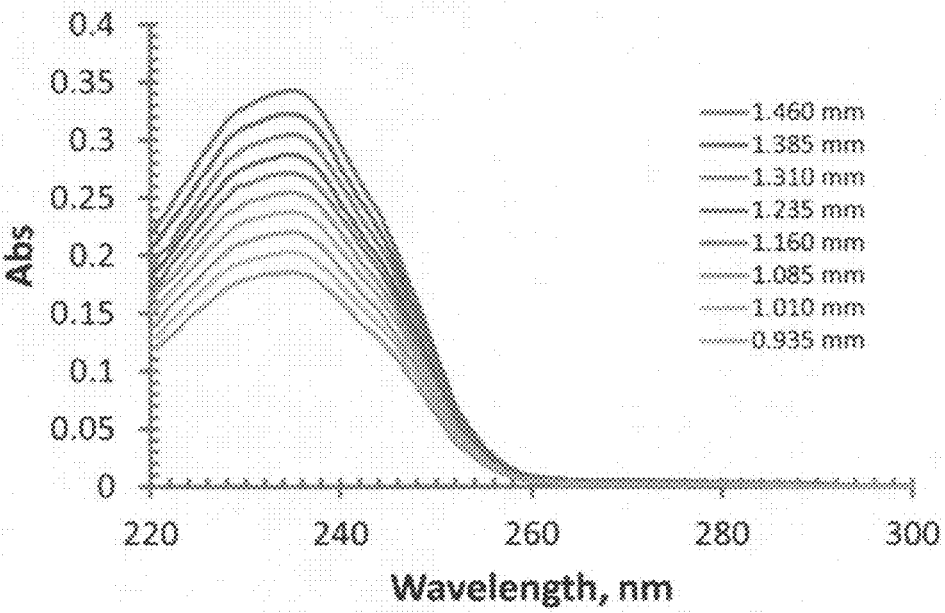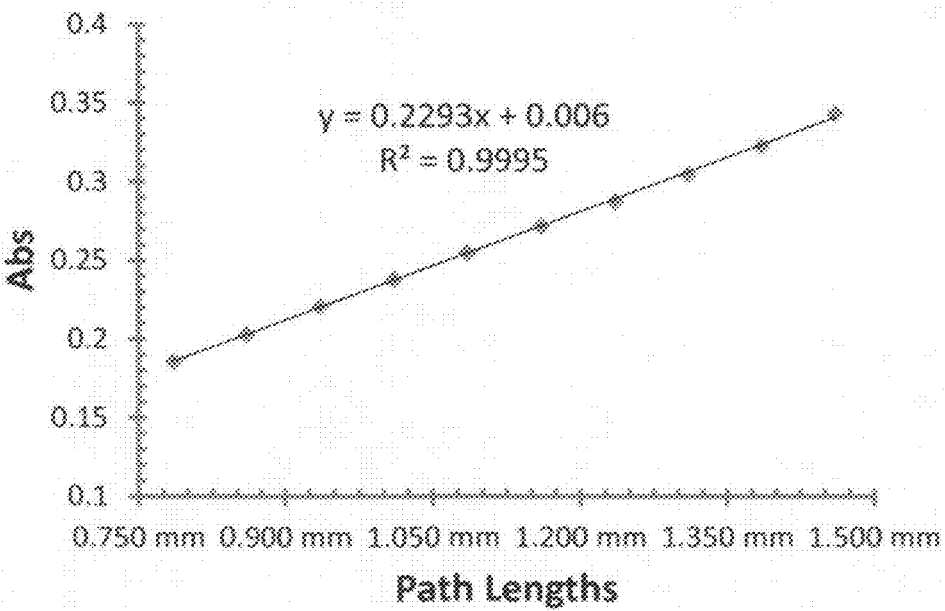

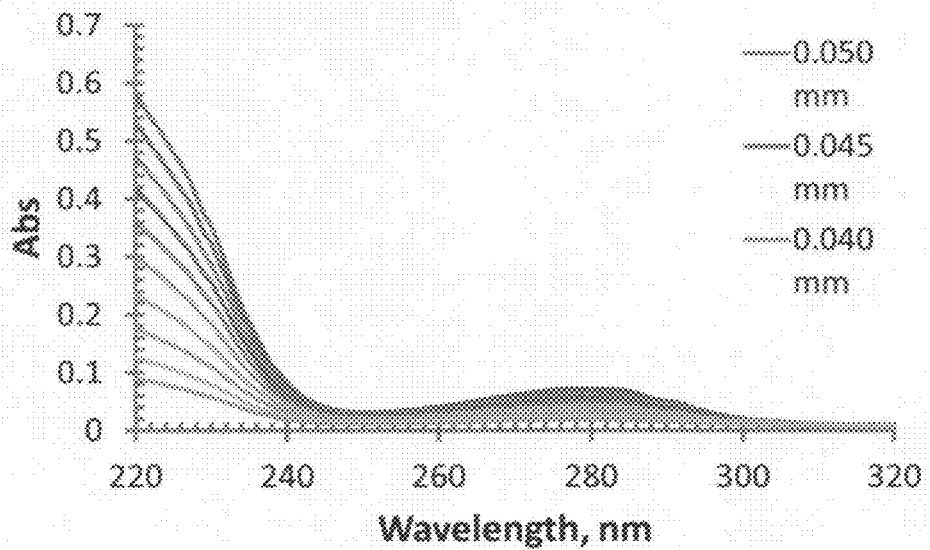
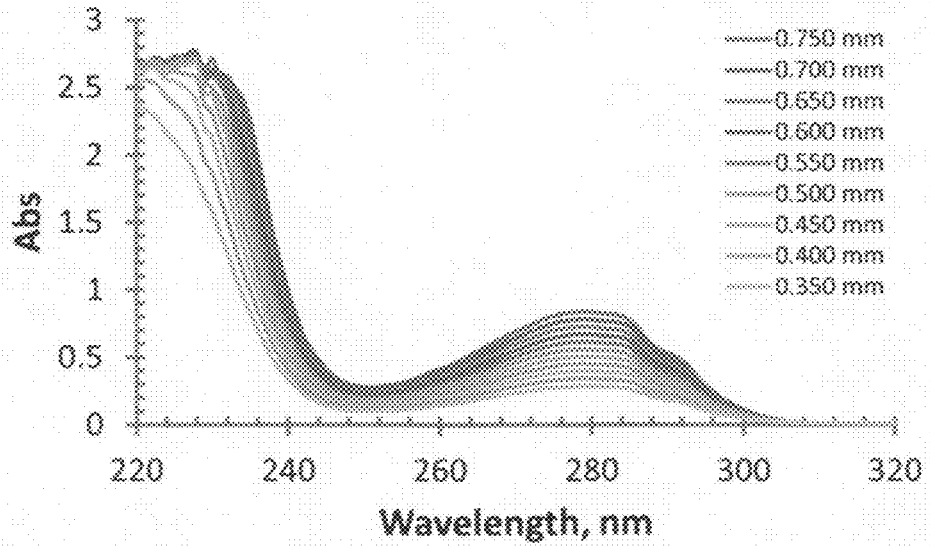

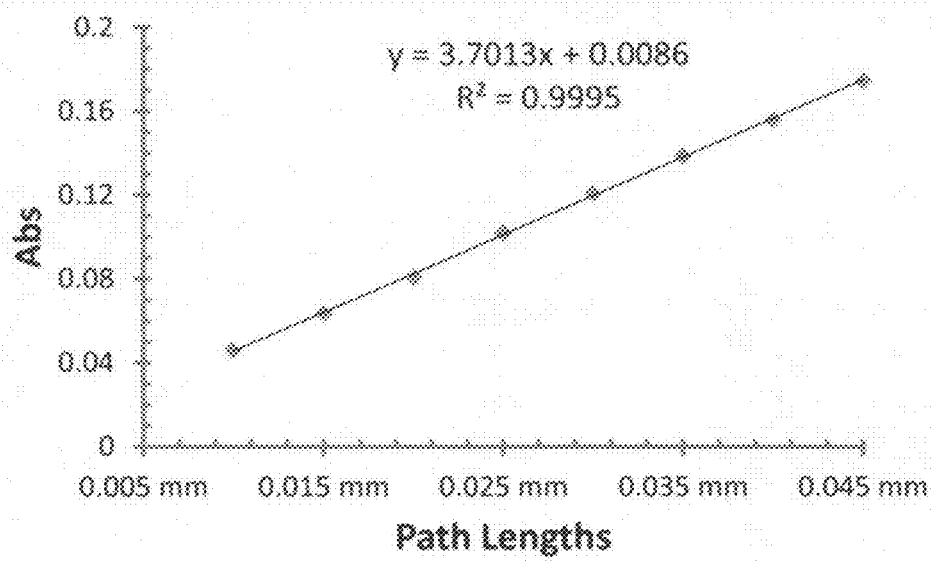
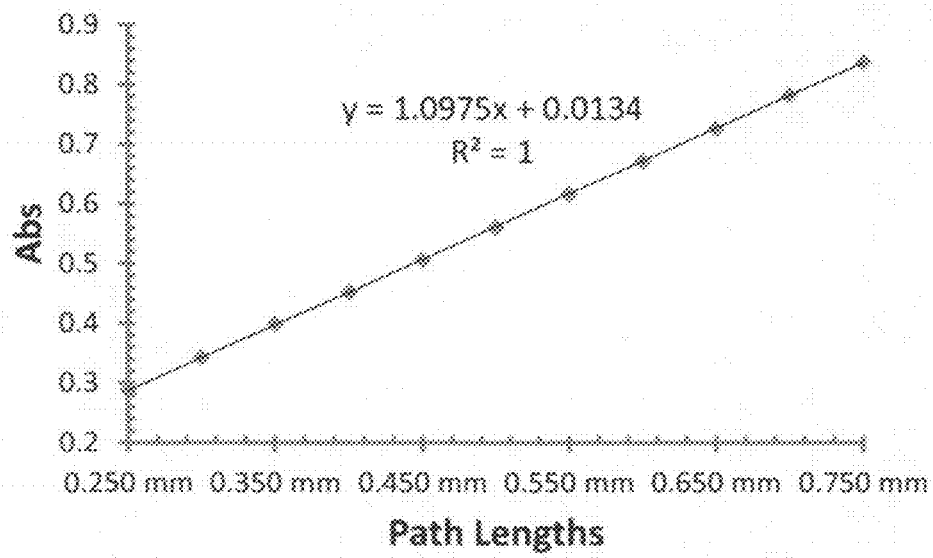

METHOD FOR QUANTITATIVELY MEASURING THE CONCENTRATION OF A COMPOUND OF UNKNOWN CONCENTRATION IN SOLUTION

RELATED APPLICATIONS

This application claims priority to U.S. Provisional Application Ser. No. 61/998,833 filed Jul. 9, 2014, which is hereby incorporated in its entirety into this application.

BACKGROUND

1. Field of the Invention

The present invention relates to methods of spectrophotometric determination of the presence of particular substances in a complex mixture of compounds. This invention relates to methods for determining the concentration of various components of complex biological samples including the determination of the concentration of polyoxyethylene containing compounds including polysorbate in protein containing samples as well as determining the ratio of drug to antibody ratios in antibody-drug conjugate solutions.

2. Description of the Related Art

Many compositions in the food, cosmetic and pharmaceutical industries are comprised of complex mixtures of organic molecules. For example, polysorbate is a common ingredient used in various industries including the pharmaceutical industry where it is used to stabilize drugs, including biologicals. Recent research works indicate consumption of polysorbate could cause problems in the human health, such as heart problems, infertility, blood clotting, and high blood pressure (Ema, M.; Hara, H.; Matsumoto, M.; Hirata-Koizumi, M.; Hirose, A.; Kamata, E., "Evaluation of developmental neurotoxicity of polysorbate 80 in rats". Reproductive Toxicology 25 (1): 89-52, 2008; Oser, B L, Oser M., "Nutritional studies on rats on diets containing high levels of partial ester emulsifiers. I. General plan and procedures; growth and food utilization". J. Nutr. 60 (3): 367-90, November 1956; Oser, B L, Oser M., "Nutritional studies on rats of diets containing high levels of partial ester emulsifiers. II. Reproduction and lactation". J. Nutr. 60 (4): 489-505, December 1956; Gajdová M., Jakubovsky J., Války J., "Delayed effects of neonatal exposure to Tween 80 on female reproductive organs in rats". Food Chem. Toxicol. 31 (3): 183-90, March 1993; Williams, J, Odum J, Lewis R W, Brady A M., "The oral administration of polysorbate 80 to the immature female rat does not increase uterine weight". Toxicol. Lett. 91 (1): 19-24, March 1997). This research has attracted the attention of both EU and USA regulatory agencies provoking discussions as to whether to monitor and regulate the content of polysorbate in the drug.

Current pharmaceutical industries standards permit polysorbate to be used in the manufacture of drugs; however, there are no standard methods to determine the exact content of polysorbate in the final drug products. The concentration of polysorbates are difficult to measure due to the fact that they are heterogeneous in nature, tend to form micelles and may bind to other components in mixtures, such as proteins, or bind to the surfaces of containers within which the polysorbates are held. Some measuring methods have been developed to determine polysorbate concentrations. (Daniel Hewitt, Taylor Zhang, Yung-Hsiang Kao, "Quantitation of polysorbate 20 in protein solutions using mixed-mode chromatography and evaporative light scattering detection", Journal of Chromatography A, Vol 1215, Issues 1-2, 26 Dec. 2008, Pages 156-160; Lakshmy, M Nair, Norma V Stephens, Sarah Vincent, Neervalur Raghavan, Patrick J Sand, "Determination of polysorbate 80 in parenteral formulations by high-performance liquid chromatography and evaporative light scattering detection", Journal of Chromatography A, Volume 1012, Issue 1, 12 Sep. 2003, Pages 81-86; Travis H. Tania, Jamie M. Mooreb, Thomas W. Patapoff, "Single step method for the accurate concentration determination of polysorbate 80", Journal of Chromatography A, Volume 786, Issue 1, 24 Oct. 1997, Pages 99-106). One such method requires retreatment of the protein sample and colorimetric determination of the content of polysorbate (Alfred Weber, Andrea Engelmaier, Heinz Anderle, Hans-Peter Schwarz, "Method For The Determination Of Polysorbate80", US Patent Publication No. 20120225487). This process involves separation, filtration, and dilution of samples, all of which is time consuming and prone to inducing errors during both sample preparation and measurement.

Antibody-drug conjugates or ADCs are a new class of highly potent biopharmaceutical drugs designed as targeted drug therapy for the treatment of people with cancer. ADCs are complex molecules composed of an antibody linked, via a stable, chemical linker with labile bonds, to a biological active cytotoxic compound. The manufacture of ADCs provides the challenge of conjugating the cytotoxic drug component to the antibody via a chemical linker in a reproducible fashion. It would be desirable to characterize the drug to antibody ratio, the amount of bound drug versus unbound drug, the amount of unbound linker and to determine the stability of the ADC both in vitro and in vivo.

Therefore, there exists a need for a method to determine the presence of particular substances in a complex mixture of compounds simply and without purification, modification or dilution. In particular, there is a need for methods which can quantitatively measure the concentration of polyoxyethylene compounds, including polysorbates, in protein samples which provide direct measurement of the samples and which do not need complicated and time consuming sample preparation. Also, there is a need to determine the concentration ratios of drug to antibody in antibody-drug conjugates (ADC).

SUMMARY OF THE INVENTION

The present invention relates to methods of determining the concentration of particular compounds in a mixture of compounds where the absorbance spectra of the compounds within the mixture may overlap making quantitation of the concentration difficult.

The present invention relates to methods of determining the concentration of surfactants in a mixture of compounds where the absorbance spectra of the compounds within the mixture may overlap making quantitation of the concentration of the surfactant difficult.

The present invention relates to methods of determining the concentration of surfactants in a mixture of compounds including proteins where the absorbance spectra of the surfactants and proteins within the mixture may overlap making quantitation of the protein and or surfactant concentration difficult.

The present invention relates to methods of determining the concentration of polysorbates in a mixture of compounds including proteins where the absorbance spectra of the polysorbates and proteins within the mixture may overlap making quantitation of the protein and or surfactant concentration difficult.

The present invention relates to methods of determining the concentration of linkers, antibodies and/or cancer treatment drugs, such as cytotoxic drugs and or antibody-conjugated drugs in a mixture of compounds. The methods of the present invention relate to the determination of drug to antibody ratios in antibody drug conjugates.

The present invention relates to methods of determining the concentration of particular compounds in a mixture of compounds where the absorbance spectra of the compounds within the mixture may overlap making quantitation of the concentration difficult. In particular, the present invention relates to methods determining the concentration of various compounds in complex solutions. The solutions may contain two or more compounds including but not limited to antibodies, drugs, surfactants, contaminants, markers and proteins. The methods of the present invention take advantage of the overlap of absorption spectra of certain components to factor out the overlapping signals so as to obtain the concentration of a compound of interest. In the simplest form, the methods can be used to determine the concentration of the two compounds in a solution where each of the compounds in the solution might absorb at one or more of the same wavelengths. For example, it is difficult to measure the concentration of a solution containing protein and polysorbate as the polysorbate absorbs at 235 nm and proteins absorb at wavelengths 235 nm and 280 nm. This means that in complex mixtures of protein and polysorbate it is not clear what each compound contributes to the absorbance measurement at 235 nm. Since proteins absorb at both 280 nm and 235 nm the ratio of the slopes of lines determined by plotting absorbance versus path length at the two different wavelengths can be used to determine the protein contribution at 235 nm and subtract it from the total absorbance at 235 nm for a solution containing protein and polysorbate, thereby enabling the calculation of the concentration of the polysorbate in the protein solution. The methods of the present invention are not limited to systems in which one compound absorbs at two wavelengths and another compound in the same solution absorbs at one of those two wavelengths. The methods of the present invention may be used to determine the concentration of various compounds in a complex solution containing many components. These components could absorb at multiple overlapping wavelengths.

The present methods may be used for determining the concentration of a compound in a solution comprising buffer and a compound by collecting a set of optical density versus wavelength spectra at two or more path lengths of the buffer of a solution as well as the solution and then the buffer spectra can be subtracted from the solution spectra to produce a compound background corrected spectra. From that spectra two or more data points at a selected first wavelength can be chosen to make a plot of absorbance versus path length to produce a first slope. This can be repeated at a second wavelength to produce a second slope and the ratio of the slopes can be calculated for the compound. Another set of optical density versus wavelength spectra at two or more path lengths of a buffer of a solution of a known the second compound as well as of a solution of known concentration of the second compound to produce a second compound background corrected spectra. Two or more data points at the first wavelength from the second compound background corrected spectra can be used to produce a slope and the extinction coefficient of the second compound can be obtained by dividing this slope by the second compound concentration. A set of optical density versus wavelength spectra at two or more path lengths of a buffer of a compound solution with an unknown concentration of the second compound as well as a spectra of a compound solution with an unknown concentration of a second compound can be used to provide a compound solution with an unknown concentration of second compound background corrected spectra whereby selecting two or more data points at a first wavelength and a second wavelength can produce two plots of absorbance versus path length each with a slope. The slope at the first wavelength for the first compound in the compounds solution with an unknown concentration of second compound can be obtained by multiplying the slope at the second wavelength of the compounds solution with an unknown concentration of second compound by the ratio of the slope obtained earlier for the first compound. The slope value at the first wavelength of the second compound in the compounds solution with an unknown concentration of second compound can be calculated by subtracting the slope at the first wavelength from the compounds solution with an unknown concentration of second compound from the slope at the first wavelength for the first compound. The concentration of second compound in the compounds solution with an unknown concentration of second compound can be obtained by dividing the slope value at the first wavelength of the second compound from the compounds solution with an unknown concentration of second compound by the extinction coefficient obtained earlier of the second compound.

BRIEF DESCRIPTION OF THE DRAWINGS

FIG. 1a is a spectra of pure protein sample for wavelength 235 nm plotted as Absorbance versus wavelength for various path lengths.

FIG. 1b is a spectra of pure protein sample for wavelength 280 nm plotted as Absorbance versus wavelength for various path lengths.

FIG. 2a is a section plot of pure protein sample at wavelength 235 nm plotted as Absorbance versus path length.

FIG. 2b is a section plot of pure protein sample at wavelength 280 nm plotted as Absorbance versus path length.

FIG. 3 is a spectra of 1.0 mg/mL polysorbate plotted as Absorbance versus wavelength for various path lengths.

FIG. 4 is a section plot of 1.0 mg/mL polysorbate at wavelength 235 nm plotted as Absorbance versus path length.

FIG. 5a is a spectra of a protein sample with unknown concentration of polysorbate for wavelength 235 nm plotted as Absorbance versus wavelength for various path lengths.

FIG. 5b is a spectra of a protein sample with unknown concentration of polysorbate for wavelength 280 nm plotted as Absorbance versus wavelength for various path lengths.

FIG. 6a is a section plot of a protein sample with unknown concentration polysorbate at wavelength 235 nm plotted as Absorbance versus wavelength for various path length.

FIG. 6b is a section plot of a protein sample with unknown concentration polysorbate at wavelength 280 nm plotted as Absorbance versus wavelength for various path length.

DETAILED DESCRIPTION OF THE INVENTION

The present invention relates to methods of determining the concentration of particular compounds in a mixture of compounds where the absorbance spectra of the compounds within the mixture may overlap making quantitation of the concentration difficult. The methods of the present invention take advantage of the overlap of absorption spectra of certain components to factor out the overlapping signals so as to obtain the concentration or ratio of concentrations of various compounds of interest. In the simplest form, a first compound in a solution of a two compounds might absorb at the same wavelength as the first compound. In more complex solutions there can be two or more different compounds some of which may have overlapping spectra. The methods of the present invention may be used to determine the concentration of the compounds in the solution as well as determine the ratio of concentration of compounds in the solution. The methods of the present invention can be used to determine the concentration of linkers, antibodies and/or cancer treatment drugs, such as cytotoxic drugs and or antibody-conjugated drugs in a mixture of compounds.

In the simplest example a solution would be made of two compounds; one compound of which absorbs at a single wavelength, $\lambda_1$, while the other compound absorbs at two wavelengths, $\lambda_1$ and $\lambda_2$. In the absorption spectrum, absorption signal peak is the result of light absorption from the solution. If different compounds in the solution absorb light at the same wavelength, the absorption peak is the summation of light absorption from all contributing compounds. It is not possible to determine the concentration of the first compound spectrophotometrically since the absorbance at $\lambda_1$ is a combination of the absorbance of both compounds. If the portion of each compound that contributes to the absorption peak can be determined, then the concentration of each compound making that contribution may be derived mathematically. Thus, because one of the components has a second absorbance wavelength, $\lambda_2$, the concentration of the first compound can be derived from the relationship between the known compound at the wavelength where the absorbances overlap, $\lambda_1$.

In one embodiment of the present invention the method is used to determine the concentration of one substance in a mixture containing at least two distinct compounds. In this example the one compound is a pure compound and the other compound is the contaminating compound. In the first step, a set of optical density measurements versus wavelength spectra at various path lengths of buffer solution which can be used in a sample containing only a pure compound and the buffer is collected.

In the next step a set of optical density versus wavelength spectra for the pure compound sample is collected. The spectra of the pure compound can then be corrected by subtracting the buffer background spectra to get the background corrected spectra of the pure compound. Data points from the background corrected spectra can be selected from two wavelengths ($\lambda_1$ and $\lambda_2$) and then plotted separately to form a line for each wavelength chosen. Linear regressions of the data set at both wavelengths can be calculated and the slope values $m_1$ and $m_2$ from the regression equations can be used to calculate the slope ratio, R, of pure compound.

$$R = \frac{m_1}{m_2}$$

In the next step collect a set of optical density versus wavelength spectra at various path lengths of the buffer for the known concentration of a second compound. The second compound may be a compound of interest such as, but not limited to, a contaminating compound. Next, a set of optical density versus wavelength spectra at various path lengths for known concentration of the contaminating compound is collected. As with the pure compound, the contaminating compound spectra can be corrected with the buffer background spectra to obtain the background corrected contaminating compound spectra. Data points from the background corrected spectra can be selected from the first wavelength (the same first wavelength as chose for the pure compound) and then plotted to form a line for each wavelength chosen. Linear regression of the data set at the first wavelengths can be calculated and using the slope spectroscopy equation, the contaminating compound extinction coefficient, $E_1$, can be derived by dividing slope value at the first wavelength, $\lambda_1$, to the known contaminating compound concentration, c.

$$E_1 = m_1/c$$

In the next step, collect a set of optical density versus wavelength spectra at various path lengths of buffer of sample of the mixture which contains a pure compound sample with an unknown concentration of contaminating compound.

Then, collect a set of optical density versus wavelength spectra at various path lengths for the pure compound sample with the unknown concentration of contaminant Correct this spectrum with the background spectra of the buffer of sample of the mixture which contains a pure compound sample with an unknown concentration of contaminating compound and obtain the background corrected spectra of the buffer of sample of the mixture which contains a pure compound sample with an unknown concentration of contaminating compound. Select data points at $\lambda_1$ and $\lambda_2$ and conduct linear regressions the data set at $\lambda_1$ and $\lambda_2$. The slope values $M_{\lambda 1}$ and $M_{\lambda 2}$ are from the regression equations at $\lambda_1$ and $\lambda_2$ respectively.

Next, determine the slope value of pure compound at $\lambda_1$, $M_{p\lambda 1}$, by multiplying slope value at $\lambda_2$, $M_{\lambda 2}$, to the slope ratio, R, $$M_{p\lambda 1} = M_{\lambda 2} \times R$$

The slope value of the contaminant at $\lambda_1$, $M_{PS\lambda 1}$, in the sample can be calculated by subtracting $M_{p\lambda 1}$ from $M_{\lambda 1}$.

$$M_{PS\lambda 1} = M_{\lambda 1} - M_{p\lambda 1}$$

The concentration of the contaminant, C, in the mixture sample can then be calculated by dividing slope value $M_{PS\lambda 1}$ by extinction coefficient of contaminant, $E_1$.

$$C = \frac{M_{PS\lambda 1}}{E_1}$$

The present invention relates to methods of determining the concentration of particular compounds in a mixture of compounds where the absorbance spectra of the compounds within the mixture may overlap making quantitation of the concentration difficult. Such a situation may occur when there is a mixture of compounds in a solution where one of the components is a contaminant. For example, polyoxyethylene containing compounds are used in a variety of industries. One type of polyoxyethylene containing compound is polysorbates which are a class of emulsifiers or surfactants used in some pharmaceuticals and food preparation. They are often used in cosmetics to solubilize essential oils into water-based products. Polysorbates are oily liquids derived from PEG-ylated sorbitan (a derivative of sorbitol) esterified with fatty acids. The polyoxyethylene portion of the molecule may have repeating monomer units from 2-200. Fatty acids attached to the PEG-ylated sorbitan include but are not limited to monolaurate, monopalmitate, monooleate, etc. Often it is necessary to determine the concentration of these compounds in a mixture of compounds, a mixture which often contains proteins. The method disclosed in the present invention may include a pure protein sample which does not contain polysorbate, a polysorbate only and known polysorbate concentration sample, and a protein sample with unknown polysorbate concentration.

The method can be performed using any spectrophotometer which enables the alteration of the path-length of the light. The methods of the present invention include but are not limited to use variable path-length instruments—specifically, SoloVPE (Salerno, I-Tsung Shih, Craig Harrison, "Interactive Variable Pathlength Device", U.S. Pat. No. 7,808,641) and Slope Spectroscopy techniques (Eric, Salerno, Mark. "The Power of Slope Spectroscopy" February 2008). These devices and methods are used for determining the spectrophotometric characteristics of a solution by employing an approach that permits the use of a variable path length for multiple determinations of the parameters of interest. For example, in determining the concentration of a compound in solution these methods and devices can determine the absorbance of a solution at various path lengths. The values of the absorbance at various path lengths can then be used to calculate the concentration of the compound in the solution. These devices and methods are particularly useful for determining the concentration of highly concentrated samples without resorting to single or multiple dilutions of the samples. This attribute is possible due to the small path lengths which the devices can achieve. The instruments can be used to measure the concentration of very concentrated samples by providing path lengths around 0.2 µm and longer. These devices and methods expand the dynamic range of a standard spectrophotometer by permitting a wide range of path lengths for measuring the absorbance values of a solution. This broad dynamic range enables users to determine the concentrations of their samples without altering (diluting or concentrating) the samples.

The methods of the present invention may be applied to more complex solutions where the concentration of other compounds, often contaminants, may be determined. Thus, the methods of the present invention may also be applied to more complex solutions in which there are more than two compounds, the concentration of which is unknown for each of the compounds. The methods of the present invention may also be applied to more complex solutions in which there are more than two compounds, the concentration of which is unknown for some of the compounds.

Solutions containing more than two, more than three, more than four, more than five, more than six, more than seven, more than eight, more than nine or more than ten may be analyzed for the concentration of one or all of the compounds in the solution or analyzed for the concentration ratio of one compound to another. Solutions with 2 to 10, or 2 to 20, or 2 to 30, or 2 to 40, or 2 to 50, or 2 to 60, or 2 to 70, or 2 to 80, or 2 to 90, or 2 to 100, or 2 to 500, or 2 to 1000, with 3 to 10, or 3 to 20, or 3 to 30, or 3 to 40, or 3 to 50, or 3 to 60, or 3 to 70, or 3 to 80, or 3 to 90, or 3 to 100, or 3 to 500, or 3 to 1000, with 4 to 10, or 4 to 20, or 4 to 30, or 4 to 40, or 4 to 50, or 4 to 60, or 4 to 70, or 4 to 80, or 4 to 90, or 4 to 100, or 4 to 500, or 4 to 1000, with 5 to 10, or 5 to 20, or 5 to 30, or 5 to 40, or 5 to 50, or 5 to 60, or 5 to 70, or 5 to 80, or 5 to 90, or 5 to 100, or 5 to 500, or 5 to 1000 may be analyzed for the concentration of one or all of the compounds in the solution or analyzed for the concentration ratio of one compound to another. For example, there may be a protein solution in which a polysorbate compound and another compound of interest are also present, both of which absorb at a wavelength at which the protein also absorbs. The same principles that apply to the methods for a two component system can be applied to this situation to determine the concentration of the polysorbate and the other compound of unknown concentration.

EXAMPLE

Example 1

Determination of Polysorbate Concentration in a Protein Solution

In step (a) a set of optical density versus wavelength spectra at various path lengths, 0.01 mm to 0.05 mm and 0.1 mm to 0.2 mm, of buffer of pure protein sample were collected. Step (b), a set of optical density vs. wavelength spectra for pure protein sample was collected at same path lengths. The current protein spectra were corrected using the background spectra in Step (a) to obtain the background corrected spectra for the protein as (FIG. 1a & 1b). Nine data points from FIG. 1a were collected at 235 nm and then plotted to form a section plot (FIG. 2a). Eleven data points from FIG. 1b were collected at 280 nm and then plotted to form a section plot (FIG. 2b). The data sets at 235 nm and at 280 nm were subject to linear regression. Using the slope values $m_{235}$ and $m_{280}$ from the regression equations at 235 nm and 280 nm respectively the slope ratio, R, of pure protein was calculated.

$$R = \frac{m_{235}}{m_{280}} = \frac{11.85}{3.553} = 3.335$$

Step (c) a set of optical density versus wavelength spectra at 0.785 mm to 1.46 mm path lengths of buffer of 1 mg/mL polysorbate only sample was collected. Step (d), a set of optical density versus wavelength spectra at same path lengths for a 1.0 mg/mL polysorbate sample was collected. The polysorbate spectrum was corrected with the background spectra in step (c) and to obtain the background corrected polysorbate only spectra (FIG. 3). Ten data points from FIG. 3 at wavelength 235 nm were selected and then plotted in the form of the section plot (FIG. 4). Linear regression was performed on the data set at 235 nm in FIG. 4. Using the slope spectroscopy equation, the 1.0 mg/mL polysorbate extinction coefficient, $E_{PS235}$, was derived by dividing slope value at 235 nm, $M_{PS235}$, to the known polysorbate concentration, c.

$$E_{PS235} = \frac{m_{PS235}}{c} = \frac{0.229}{1.0} = 0.229$$

In Step (e), a set of optical density versus wavelength spectra at various path lengths, 0.25 mm to 0.75 mm and 0.01 mm to 0.045 mm, of buffer of protein sample with unknown concentration of polysorbate was collected. Step (f), collected a set of optical density versus wavelength spectra at same path lengths for the protein sample with an unknown concentration of polysorbate. This spectrum was corrected with the background spectra in Step (e) and to obtain the background corrected spectra as seen in FIGS. 5a & 5b. Eight data points at 235 nm and 280 nm wavelengths were selected from FIG. 5a to form the section plot (FIG. 6a). Eleven data points at 280 nm wavelengths were selected from FIG. 5b to form the section plot (FIG. 6b). Linear regression was performed on the data set at 235 nm and data set at 280 nm in FIGS. 6a & 6b. The slope values $M_{235}$ and $M_{280}$ were obtained from the regression equations at 235 nm and 280 nm respectively.

The slope value of protein at 235 nm, $M_{p235}$, was determined by multiplying slope value at 280 nm, $M_{280}$, to the Slope ratio, R, in step (b).

$$M_{p235} = M_{280} \times R = 1.098 \times 3.335 = 3.662$$

The slope value of polysorbate at 235 nm, $M_{PS235}$, in the sample used in step (f) was determined by subtracting $M_{p235}$ from $M_{235}$.

$$M_{PS235} = M_{235} - M_{p235} = 3.701 - 3.662 = 0.039$$

Finally, the concentration of polysorbate, C, in the sample used in step (f) was then calculated by multiplying extinction coefficient of polysorbate, $E_{PS235}$, to slope value $M_{PS235}$.

$$C = \frac{M_{PS235}}{E_{PS235}} = \frac{0.039}{0.229} = 0.17 \text{ mg/mL}$$

Example 2

Determination of Drug to Antibody Concentration Ratio in an ADC Samples

Step (a) a set of optical density versus wavelength spectra at various path lengths of buffer of drug only sample were collected. Step (b), a set of optical density vs. wavelength spectra of drug only sample was collected at same path lengths. The current drug only sample spectra were corrected using the background spectra in Step (a) to obtain the background corrected spectra for the drug only sample. Data points from background corrected spectra were collected at wavelengths $\lambda_1$ and $\lambda_2$ and then plotted to form section plots. The data sets at wavelengths $\lambda_1$ and $\lambda_2$ were subject to linear regression. The slope values, $m_{Drug,\lambda1}$ and $M_{Drug\lambda2}$, are from the regression equations at $\lambda_1$ and $\lambda_2$ respectively. Using the slope spectroscopy equation, the slope values of drug only sample have following relationship $$\frac{m_{Drug,\lambda1}}{E_{Drug,\lambda1}} = \frac{m_{Drug,\lambda2}}{E_{Drug,\lambda2}}$$

Where $E_{Drug,\lambda1}$ and $E_{Drug,\lambda2}$ are the extinction coefficients of drug only sample at wavelengths $\lambda_1$ and $\lambda_2$ respectively.

Using same steps mentioned above for Antibody only sample, the slope values, $M_{AB,\lambda1}$ and $m_{AB,\lambda2}$, are from the regression equations of section plots at $\lambda_1$ and $\lambda_2$ respectively. Using the slope spectroscopy equation, the slope values of Antibody only sample have following relationship $$\frac{m_{AB,\lambda1}}{E_{AB,\lambda1}} = \frac{m_{AB,\lambda2}}{E_{AB,\lambda2}}$$

Where $E_{AB,\lambda1}$ and $E_{AB,\lambda2}$ are the extinction coefficients of drug only sample at wavelengths $\lambda_1$ and $\lambda_2$ respectively.

Using same steps mentioned above for ADC sample, the slope values, $m_{\lambda1}$ and $m_{\lambda2}$, are from the regression equations of section plots at $\lambda_1$ and $\lambda_2$ respectively. The drug concentration, $C_{Drug}$, to Antibody Concentration, $C_{AB}$, ratio in ADC sample can then be derived from following equation.

$$C_{Drug}/C_{AB} = (m_{\lambda1} \cdot E_{AB,\lambda2} - m_{\lambda2} \cdot E_{AB,\lambda1})/(m_{\lambda2} \cdot E_{Drug,\lambda1} - m_{\lambda1} \cdot E_{Drug,\lambda2})$$

Within this disclosure, any indication that a feature is optional is intended provide adequate support (e.g., under 35 U.S.C. 112 or Art. 83 and 84 of EPC) for claims that include closed or exclusive or negative language with reference to the optional feature. Exclusive language specifically excludes the particular recited feature from including any additional subject matter. For example, if it is indicated that A can be drug X, such language is intended to provide support for a claim that explicitly specifies that A consists of X alone, or that A does not include any other drugs besides X. "Negative" language explicitly excludes the optional feature itself from the scope of the claims. For example, if it is indicated that element A can include X, such language is intended to provide support for a claim that explicitly specifies that A does not include X. Non-limiting examples of exclusive or negative terms include "only," "solely," "consisting of," "consisting essentially of," "alone," "without", "in the absence of (e.g., other items of the same type, structure and/or function)" "excluding," "not including", "not", "cannot," or any combination and/or variation of such language.

Similarly, referents such as "a," "an," "said," or "the," are intended to support both single and/or plural occurrences unless the context indicates otherwise. For example "a dog" is intended to include support for one dog, no more than one dog, at least one dog, a plurality of dogs, etc. Non-limiting examples of qualifying terms that indicate singularity include "a single", "one," "alone", "only one," "not more than one", etc. Non-limiting examples of qualifying terms that indicate (potential or actual) plurality include "at least one," "one or more," "more than one," "two or more," "a multiplicity," "a plurality," "any combination of," "any permutation of," "any one or more of," etc. Claims or descriptions that include "or" between one or more members of a group are considered satisfied if one, more than one, or all of the group members are present in, employed in, or otherwise relevant to a given product or process unless indicated to the contrary or otherwise evident from the context.

Where ranges are given herein, the endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While this invention has been particularly shown and described with references to example embodiments thereof, it will be understood by those skilled in the art that the various changes in form and details may be made therein without departing from the scope of the invention encompassed by the appended claims.

The invention claimed is:

1. A method for determining the concentration of a second compound in a solution comprising buffer and a first compound and a second compound comprising:
   a. collecting a set of optical density versus wavelength spectra at two or more path lengths of the buffer of a solution containing first compound only to produce a first buffer background spectra;
   b. collecting a set of optical density versus wavelength spectra at two or more path lengths for the solution containing first compound only;
   c. correcting the solution containing first compound spectra with the first buffer background spectra to produce a first compound background corrected spectra;
   d. selecting two or more data points at a first wavelength from the first compound background corrected spectra and performing linear regression on the data points to produce a first slope;
   e. selecting two or more data points at a second wavelength from the first compound background corrected spectra and performing linear regression on the data point to produce a second slope;

f. calculating the ratio of the slopes at the first and second wavelengths for the first compound;

g. collecting a set of optical density versus wavelength spectra at two or more path lengths of a buffer of a solution containing a known concentration of the second compound only to produce a second buffer background spectra;

h. collecting a set of optical density versus wavelength spectra at two or more path lengths of a solution containing a known concentration of the second compound only;

i. correcting the known concentration of the second compound solution spectra with the second buffer background spectra to produce a known concentration of the second compound background corrected spectra;

j. selecting two or more data points at the first wavelength from the known concentration of the second compound background corrected spectra and performing linear regression on the data points to produce a third slope;

k. determining the extinction coefficient of the second compound by dividing the third slope by the second compound concentration;

l. collecting a set of optical density versus wavelength spectra at two or more path lengths of a buffer of a solution with unknown concentrations of the first and second compounds to produce a third buffer background spectra;

m. collecting a set of optical density versus wavelength spectra at two or more path lengths for solution with unknown concentrations of the first and second compounds;

n. correcting the solution with unknown concentrations of the first and second compounds spectra with the third buffer background spectra to produce a background corrected spectra for a solution with unknown concentration of the first and second compounds;

o. selecting two or more data points at a first wavelength from background corrected spectra of solution with unknown concentrations of the first and second compounds and performing linear regression on the data point to produce a fourth slope;

p. selecting two or more data points at a second wavelength from the background corrected spectra of solution with unknown concentrations of the first compound and second compounds and performing linear regression on the data points to produce a fifth slope;

q. calculating the slope at the first wavelength for the first compound in the solution with unknown concentrations of the first and second compounds by multiplying the fifth slope to the ratio of the slopes at the first and second wavelengths of the first compound;

r. determining the slope value at the first wavelength of the second compound in the solution with unknown concentrations of the first and second compounds by subtracting the slope at the first wavelength of the first compound in the solution with unknown concentrations of the first and second compounds from the fourth slope; and s. determining the concentration of the second compound in the solution with unknown concentrations of the first and second compounds by dividing the slope value of the second compound in the solution with unknown concentrations of the first and second compounds by the extinction coefficient at the first wavelength of the second compound.

2. The method of claim 1 wherein there are more than two compounds in the solution comprising a first compound and a second compound.

3. A method for determining the concentration of polyoxyethylene containing surfactants in a solution comprising buffer and protein and polyoxyethylene containing surfactants comprising:

a. collecting a set of optical density versus wavelength spectra at two or more path lengths of the buffer of a pure protein solution to produce a first buffer background spectra;

b. collecting a set of optical density versus wavelength spectra at two or more path lengths for the pure protein solution;

c. correcting the pure protein spectra with the first buffer background spectra to produce a protein background corrected spectra;

d. selecting two or more data points at a first wavelength from the protein background corrected spectra and performing linear regression on the data points to produce a first slope;

e. selecting two or more data points at a second wavelength from the protein background corrected spectra and performing linear regression on the data point to produce a second slope;

f. calculating the ratio of the slopes at the first and second wavelengths for the pure protein solution;

g. collecting a set of optical density versus wavelength spectra at two or more path lengths of a buffer of a solution of known concentration of polyoxyethylene to produce a second buffer background spectra;

h. collecting a set of optical density versus wavelength spectra at two or more path lengths for a known concentration of polyoxyethylene solution;

i. correcting the known concentration of polyoxyethylene solution spectra with the second buffer background spectra to produce a known concentration of polyoxyethylene solution background corrected spectra;

j. selecting two or more data points at the first wavelength from the known concentration of polyoxyethylene solution background corrected spectra and performing linear regression on the data point to produce a third slope;

k. determining the extinction coefficient of the polyoxyethylene by dividing the third slope by the polyoxyethylene concentration;

l. collecting a set of optical density versus wavelength spectra at two or more path lengths of the buffer of a protein solution with an unknown concentration of polyoxyethylene and unknown concentration of protein to produce a third buffer background spectra;

m. collecting a set of optical density versus wavelength spectra at two or more path lengths for the protein solution with an unknown concentration of polyoxyethylene and unknown concentration of protein;

n. correcting the protein solution with an unknown concentration of polyoxyethylene and unknown concentration of protein spectra with the third buffer background spectra to produce a protein solution with an unknown concentration of polyoxyethylene and unknown concentration of protein background corrected spectra;

o. selecting two or more data points at a first wavelength from the protein solution with an unknown concentration of polyoxyethylene and unknown concentration of protein background corrected spectra and performing linear regression on the data point to produce a fourth slope;

p. selecting two or more data points at a second wavelength from the protein solution with an unknown concentration of polyoxyethylene and unknown concentration of protein background corrected spectra and performing linear regression on the data point to produce a fifth slope;

q. calculating the slope at the first wavelength for the protein in the solution with an unknown concentration of polyoxyethylene and unknown concentration of protein by multiplying the fifth slope by the ratio of the slopes at the first and second wavelengths for the pure protein;

r. determining the slope value of the polyoxyethylene in the protein solution with an unknown concentration of polyoxyethylene and unknown concentration of protein by subtracting the slope from the pure protein in the protein solution with an unknown concentration of polyoxyethylene and unknown concentration of protein from the fourth slope; and s. determining the concentration of the polyoxyethylene in the protein solution with an unknown concentration of polyoxyethylene and unknown concentration of protein by dividing the slope value of the polyoxyethylene in the protein solution with an unknown concentration of polyoxyethylene and unknown concentration of protein by the extinction coefficient at the first wavelength of the polyoxyethylene.

4. The method of claim 3 wherein the polyoxyethylene is polysorbate.

5. The method of claim 4 wherein the polyoxyethylene is polysorbate 80.

6. The method of claim 5 wherein the first wavelength is approximately 235 nm.

7. The method of claim 6 wherein the second wavelength is approximately 280 nm.

8. The method of claim 4 wherein the first wavelength is approximately 235 nm.

9. The method of claim 8 wherein the second wavelength is approximately 280 nm.

10. The method of claim 3 wherein the collection of the optical density versus wavelength spectra at two or more path lengths is conducted by a variable path-length instrument.

11. The method of claim 10 wherein the variable path-length instrument is a Solo VPE.

12. A method for determining the concentration ratio of antibody to drug in a solution comprising an antibody and drug comprising:

a. collecting a set of optical density versus wavelength spectra at two or more path lengths of the buffer of the pure drug to produce a first buffer background spectra;

b. collecting a set of optical density versus wavelength spectra at two or more path lengths for the pure drug;

c. correcting the pure drug spectra with the first buffer background spectra to produce a pure drug background corrected spectra;

d. selecting two or more data points at a first wavelength from the pure drug background corrected spectra and performing linear regression on the data points to produce a first slope ($m_{drug,\lambda 1}$);

e. selecting two or more data points at a second wavelength from the pure drug background corrected spectra and performing linear regression on the data point to produce a second slope ($m_{drug,\lambda 2}$);

f. calculating an extinction coefficient for the drug at the second wavelength ($E_{drug,\lambda 2}$) by multiplying an extinction coefficient at the first wavelength ($E_{drug,\lambda 1}$) by the second slope ($m_{drug,\lambda 2}$) divided by the first slope ($m_{drug,\lambda 1}$);

g. collecting a set of optical density versus wavelength spectra at two or more path lengths of a buffer of a solution of antibody to produce a second buffer background spectra;

h. collecting a set of optical density versus wavelength spectra at two or more path lengths for an antibody solution;

i. correcting the antibody solution spectra with the second buffer background spectra to produce an antibody corrected spectra;

j. selecting two or more data points at the first wavelength from the antibody background corrected spectra and performing linear regression on the data points to produce a third slope ($m_{AB,\lambda 1}$);

k. selecting two or more data points at the second wavelength from the antibody background corrected spectra and performing linear regression on the data points to produce a fourth slope ($m_{AB,\lambda 2}$);

l. calculating an extinction coefficient for the antibody at the second wavelength ($E_{AB,\lambda 2}$) by multiplying an extinction coefficient at the first wavelength ($E_{AB,\lambda 1}$) by the fourth slope ($m_{AB,\lambda 2}$); divided by the third slope ($m_{AB,\lambda 1}$);

m. collecting a set of optical density versus wavelength spectra at two or more path lengths of a buffer of a solution with an unknown concentration of drug and antibody to produce a third buffer background spectra;

n. collecting a set of optical density versus wavelength spectra at two or more path lengths for a solution with an unknown concentration of drug and antibody;

o. correcting the pure protein spectra with the third buffer background spectra to produce a solution with an unknown concentration of drug and antibody background corrected spectra;

p. selecting two or more data points at a first wavelength from the solution with an unknown concentration of drug and antibody background corrected spectra and performing linear regression on the data point to produce a fifth slope ($m_{\lambda 1}$);

q. selecting two or more data points at a second wavelength from the solution with an unknown concentration of drug and antibody background corrected spectra and performing linear regression on the data points to produce a sixth slope ($m_{\lambda 2}$);

r. calculating the ratio of drug to antibody concentration ($C_{drug}/C_{AB}$) by dividing the result of subtracting the product of sixth slope ($m_{\lambda 2}$) and the extinction coefficient ($E_{AB,\lambda 1}$) of the antibody at the first wavelength from the product of fifth slope ($m_{\lambda 1}$) and extinction coefficient ($E_{AB,\lambda 2}$) of the antibody at the second wavelength by the result of subtracting the product of fifth slope ($m_{\lambda 1}$) and the extinction coefficient ($E_{Drug,\lambda 1}$) of the drug at the first wavelength from the product of sixth slope ($m_{\lambda 2}$) and extinction coefficient ($E_{Drug,\lambda 2}$) of the drug at the second wavelength wherein $$C_{drug}/C_{AB} = (m_{\lambda 1} \times E_{AB,\lambda 2} \times E_{AB,\lambda 1})/(m_{\lambda 2} \times E_{drug,\lambda 2} - m_{\lambda 1} \times E_{drug,\lambda 1}).$$

13. A method for determining the concentration ratio of a first compound to a second compound in a solution comprising two or more compounds comprising:

a. collecting a set of optical density versus wavelength spectra at two or more path lengths of the buffer of a solution with the first compound only to produce a first buffer background spectra;

b. collecting a set of optical density versus wavelength spectra at two or more path lengths for the solution with the first compound only;
c. correcting the solution with the first compound only spectra with the first buffer background spectra to produce a first compound background corrected spectra;
d. selecting two or more data points at a first wavelength from the first compound background corrected spectra and performing linear regression on the data points to produce a first slope ($m_{C1,\lambda1}$);
e. selecting two or more data points at a second wavelength from the first compound background corrected spectra and performing linear regression on the data point to produce a second slope ($m_{C1,\lambda2}$);
f. calculating an extinction coefficient for the first compound at the second wavelength ($E_{C1,\lambda2}$) by multiplying an extinction coefficient at the first wavelength ($E_{C1,\lambda1}$) by the second slope ($m_{C1,\lambda2}$) divided by the first slope ($m_{C1,\lambda1}$);
g. collecting a set of optical density versus wavelength spectra at two or more path lengths of the buffer of a solution with the second compound only to produce a second buffer background spectra;
h. collecting a set of optical density versus wavelength spectra at two or more path lengths for the solution with the second compound only;
i. correcting the solution with the second compound only spectra with the second buffer background spectra to produce a second compound background corrected spectra;
j. selecting two or more data points at a first wavelength from the second compound background corrected spectra and performing linear regression on the data points to produce a third slope ($m_{C2,\lambda1}$);
k. selecting two or more data points at a second wavelength from the second compound background corrected spectra and performing linear regression on the data point to produce a fourth slope ($m_{C2,\lambda2}$);
l. calculating an extinction coefficient for the second compound at the second wavelength ($E_{C2,\lambda2}$) by multiplying an extinction coefficient at the first wavelength ($E_{C2,\lambda1}$) by the fourth slope ($m_{C2,\lambda2}$) divided by the third slope ($m_{C2,\lambda1}$);
m. collecting a set of optical density versus wavelength spectra at two or more path lengths of a buffer of a solution containing the first and second compounds to produce a third buffer background spectra;
n. collecting a set of optical density versus wavelength spectra at two or more path lengths for a solution containing the first and second compounds;
o. correcting the solution containing the first and second compounds spectra with the third buffer background spectra to produce a solution with the first and second compounds background corrected spectra;
p. selecting two or more data points at a first wavelength from the solution with the first and second compounds background corrected spectra and performing linear regression on the data point to produce a fifth slope ($m_{\lambda1}$);
q. selecting two or more data points at a second wavelength from the solution with the first and second compounds background corrected spectra and performing linear regression on the data points to produce a sixth slope ($m_{\lambda2}$);
r. calculating the concentration ratio of the first compound to the second compound ($C_{C1}/C_{C2}$) by dividing the result of subtracting the product of fifth slope ($m_{\lambda1}$) and extinction coefficient ($E_{C2,\lambda2}$) of the second compound at the second wavelength to the product of sixth slope ($m_{\lambda2}$) and the extinction coefficient ($E_{C2,\lambda1}$) of the second compound at the first wavelength to the result of subtracting the product of sixth slope ($m_{\lambda2}$) and extinction coefficient ($E_{C1,\lambda2}$) of the first compound at the second wavelength to the product of fifth slope ($m_{\lambda1}$) and the extinction coefficient ($E_{C1,\lambda1}$) of the first compound at the first wavelength wherein $$C_{C1}/C_{C2} = (m_{\lambda1} \times E_{C2,\lambda2} - m_{\lambda2} \times E_{C2,\lambda1})/(m_{\lambda2} \times E_{C1,\lambda2} - m_{\lambda1} \times E_{C1,\lambda1}).$$

14. The method of claim 13 wherein there are more than two compounds in the solution comprising two or more compounds.

* * * * *